(12) United States Patent
Bova et al.

(10) Patent No.: US 7,651,506 B2
(45) Date of Patent: Jan. 26, 2010

(54) FRAMELESS STEREOTACTIC GUIDANCE OF MEDICAL PROCEDURES

(75) Inventors: Frank Joseph Bova, Gainesville, FL (US); William Allen Friedman, Gainesville, FL (US)

(73) Assignee: University of Florida Research Foundation, Inc., Gainesville, FL (US)

(*) Notice: Subject to any disclaimer, the term of this patent is extended or adjusted under 35 U.S.C. 154(b) by 0 days.

(21) Appl. No.: 11/400,015

(22) Filed: Apr. 7, 2006

(65) Prior Publication Data

US 2006/0212044 A1 Sep. 21, 2006

Related U.S. Application Data

(63) Continuation-in-part of application No. 10/677,419, filed on Oct. 2, 2003, now abandoned.

(51) Int. Cl.
*A61B 19/00* (2006.01)
(52) U.S. Cl. .................. 606/130; 606/167; 606/172; 600/407; 600/425; 600/427
(58) Field of Classification Search ............ 606/130, 606/167, 172; 600/407, 425, 427
See application file for complete search history.

(56) References Cited

U.S. PATENT DOCUMENTS

| | | | | |
|---|---|---|---|---|
| 4,613,324 | A * | 9/1986 | Ghajar | 604/539 |
| 4,957,124 | A * | 9/1990 | Mooney | 132/200 |
| 5,375,588 | A * | 12/1994 | Yoon | 600/114 |
| 5,663,646 | A | 9/1997 | Kuth et al. | |
| 5,676,673 | A | 10/1997 | Ferre et al. | |
| 5,768,134 | A | 6/1998 | Swaelens et al. | |
| 5,873,822 | A * | 2/1999 | Ferre et al. | 600/407 |
| 6,122,541 | A | 9/2000 | Cosman et al. | |
| 6,282,437 | B1 * | 8/2001 | Franck et al. | 600/429 |
| 6,327,491 | B1 * | 12/2001 | Franklin et al. | 600/429 |
| 6,332,891 | B1 * | 12/2001 | Himes | 606/169 |
| 7,024,237 | B1 * | 4/2006 | Bova et al. | 600/429 |

(Continued)

FOREIGN PATENT DOCUMENTS

WO WO 00/01316 1/2000

(Continued)

OTHER PUBLICATIONS

Birnbaum et al. "Computer-Assisted Orthopedic Surgery With Individual Templates and Comparison to Conventional Operation Method" SPINE, 2001, 26(4):365-370.

(Continued)

*Primary Examiner*—Brian Casler
*Assistant Examiner*—James Kish
(74) *Attorney, Agent, or Firm*—Thomas, Kayden, Horstemeyer & Risley LLP

(57) ABSTRACT

Devices, methods and systems for frameless guidance of image-based medical procedures such as stereotactic radiotherapy and surgery. Devices including custom fitting subject-specific articles include contoured surfaces that provide spatial reference to the location of target regions within the subject. The devices are attached exclusive of fasteners anchored to the tissue of the subject and reside on the front of a head of the subject when attached. The devices and articles can be fabricated using computer-directed fabrication technology.

16 Claims, 11 Drawing Sheets

U.S. PATENT DOCUMENTS

2003/0131852 A1\* 7/2003 Shafer et al. ........... 128/206.21

FOREIGN PATENT DOCUMENTS

WO     WO 2005/039386 A2    5/2005

OTHER PUBLICATIONS

Yoo et al. "Template Guided Intervention: Interactive Visualization and Design for Medical Fused Deposition Models" Proceedings of the Workshop on Interactive Medical Image Visualization and Image Analysis, Oct. 2001, pp. 45-48.

\* cited by examiner (A)

(B)

FRAMELESS STEREOTACTIC GUIDANCE OF MEDICAL PROCEDURES

CROSS REFERENCE TO RELATED APPLICATIONS

The present application is a continuation-in-part of application Ser. No. 10/677,419 entitled "FRAMELESS STEREOTACTIC GUIDANCE OF MEDICAL PROCEDURES" filed on Oct. 2, 2003, which is incorporated by reference in its entirety into the present application.

STATEMENT AS TO FEDERALLY SPONSORED RESEARCH

Not applicable.

FIELD OF THE INVENTION

This invention relates generally to the fields of medicine, radiology and neurosurgery. More particularly, the invention relates to methods and devices for image-guided medical procedures, such as stereotactic cranial radiation and surgery.

BACKGROUND

Many modern medical procedures, both invasive and non-invasive, are performed with the assistance of medical imaging devices. A series of two-dimensional images generated from devices such as CT or MRI scanners are used to generate virtual 3-dimensional models of regions of interest from subjects. These models are used in the planning, practice and execution of medical procedures subsequently performed on the subjects. Image-guided medical procedures are generally accomplished by coordinating 3-D virtual models of subjects with reference points on the actual subjects undergoing the medical procedures. Current approaches for image-guided medical procedures such as stereotactic biopsy or radiation therapy can be divided into two approaches. The first approach uses a rigid frame secured to the subject, such as a human patient. The second approach is a frameless approach, in which fiducial landmarks, either derived from the patient's own anatomical features or applied to the surface of the patient, are used to coordinate the 3-D virtual patient model to the real world patient.

As shown in FIG. 1, in the rigid frame approach, a stereotactic frame is rigidly attached to the patient by placing fasteners directly to the skull. A detailed 3-D image map is then created from CT, MRI, or other 3-D imaging source. Fiducial markers placed on the stereotactic frame (not shown) appear in the images and allow objects in the image to be related to the stereotactic frame. Hence, targets of interest, such as a tumor and its surrounding anatomy, can be described using the coordinates of the stereotactic frame as a reference. The patient is then transferred to the operating room for treatment, again using the stereotactic frame as a reference. A biopsy arc is attached to the frame. A target trajectory is planned, and the arc parameters required to follow the trajectory are derived. The settings are applied to the biopsy arc and the biopsy is obtained. Although this approach eliminates the error-generating step of registering the virtual model to the actual subject, this approach is invasive and is as a result uncomfortable for patients.

In the frameless approach, the registration of the patient to the image-based operative model requires the identification of fiducial markers. Some fiducials are external markers applied to the patient prior to scanning and kept in place until registration has been completed, while other reference markers are actually identifiable anatomic landmarks based on the patient's own anatomy. The identification of these fiducial points can be difficult and can add significant time to the operative procedure. Additionally, movement of the fiducials relative to internal anatomy can degrade the accuracy of the registration process and subsequently detract from the overall accuracy of the image-guided procedure.

During the operative procedure with either frame-based or frameless approaches, tracking of the patient position as well as the position of the operative instruments is generally accomplished using one of two primary tracking technologies. The most popular system is optical tracking. Optical tracking systems depend upon a line of sight between the tracking camera and the tracked object, either the surgical instrument or a patient dynamic reference. Some optical systems track active infrared light emitting diodes while other systems track passive infrared reflective spheres. The second most popular system for patient and instrument tracking is electromagnetic tracking. In an electromagnetic tracking system, an emitter is typically used as the reference and is rigidly attached to the subject. All instruments are then tracked relative to the reference emitter. When electromagnetic tracking is employed, instruments that may distort the electromagnetic field, as well as other large pieces of electronic equipment, must be kept at sufficient distance from the surgical field to avoid significant spatial error introduction.

Both types of tracking systems suffer from drawbacks. In a surgical suite with multiple surgeons, support staff and support equipment, obtaining a "clean" electromagnetic environment needed for accurate electromagnetic tracking can be difficult. In the case of optical tracking, maintaining an unobstructed view of the operative field is often problematic and can lead to inaccuracies or the inability to track.

SUMMARY

The invention provides a device for guiding medical procedures, including a subject-specific article dimensioned to follow a contour of an exterior surface portion of the head of a subject to be treated. The article is rigidly attachable to the surface portion without relying on fasteners anchored to tissue of the subject. Upon attachment to the subject, the article exclusively resides on the front of the head of the subject and provides a customized spatially unambiguous reference for alignment of a preplanned medical procedure to one or more target regions associated with the head of the subject.

In some embodiments, the article upon attachment exclusively contacts non-opposing exterior surfaces of the head of subject. In some embodiments, the article is dimensioned to follow a contour of at least one of the nose, the eye socket, the eyebrow ridge. In some embodiments, the subject-specific article of the device may be anchored to soft tissue of the head of the subject, but is attached exclusive of fasteners anchored to bone of the subject underlying the article upon attachment.

In some embodiments of the device, the article can include at least one opening for access to a surface portion of the subject, further including a probe guide emerging from the opening. In some versions of the device, the probe guide can be oriented at a predetermined angle with respect to the article, for guidance to the opening or to embedded regions under the opening aligned with the probe guide. In other embodiments, an angle of the probe guide emerging from the opening can be adjustable.

Devices of the invention can further include at least one structure for directing a biopsy or incision depth attached to the article. The article can include at least one opening for access to a surface portion, and can further include at least one surface for attachment of a custom skin clip or retractor along a periphery of the opening.

In some embodiments, the invention may include a structure for attaching the article to a stereotactic phantom device. The stereotactic phantom device is used for insuring proper alignment of the article on the head of the subject prior to performing the procedure on the subject.

In another aspect, the invention provides a method for guiding a medical procedure, including the steps of: providing a subject-specific article including at least one reference contour dimensioned to follow a contour of an exterior surface portion of the head of a subject to be treated, the article being rigidly attachable to the surface portion exclusive of fasteners anchored to tissue of the subject underlying the article upon attachment. The article upon attachment exclusively resides on the front of the subject's head and the article provides a customized spatially unambiguous reference for alignment of a preplanned medical procedure to one or more target regions associated with the head of the subject; attaching the article on the subject; and performing a medical procedure on the target region, guided at least in part by the subject-specific article. The method can be used for procedures including radiotherapy and surgery.

The inventive method may further comprise the step of checking proper alignment of the article upon attachment using a stereotactic phantom device and related procedure adapted for use with the invention, prior to using a frame for patient application. This embodiment of the invention can incorporate external reference sockets on the patient specific mask, such as a biopsy probe holder, with the reference sockets being placed at known coordinates, with the phantom device design providing a phantom base having the mating portion of the sockets.

The invention further provides a system for performing a medical procedure, including: a device including a subject-specific article including at least one reference contour dimensioned to follow a contour of an exterior surface portion of the head of a subject to be treated, the article being rigidly attachable to the surface portion exclusive of fasteners anchored to tissue of the subject underlying the article upon attachment. Upon attachment, the article exclusively resides on the front of the subject's head and provides a customized spatial reference for alignment of a preplanned medical procedure to one or more target regions of the subject; and a therapeutic, diagnostic or surgical device, wherein the device is guided to the target region at least in part by the subject-specific article.

In some versions of the system of the invention, the article can include a plurality of external reference markers. The external reference markers can be optical markers. In other embodiments, the article can include at least one opening for access to the surface portion of the subject, further including a probe guide emerging from the opening.

In yet another aspect, the invention provides a system for forming a subject-specific device for guiding a medical procedure, the system including: computing structure for providing 3-dimensional data representing a subject-specific article including at least one reference contour dimensioned to replicate a contour of an exterior surface portion of the head of a subject to be treated; and a machine for forming the article from the 3-dimensional data. The article is designed such that it is attachable to a surface portion of the subject exclusive of fasters anchored to the subject's tissue underlying the article as attached and the article upon attachment exclusively resides on the front of the subject's head. The contour of the subject to be treated can be computed from a 3-dimensional planning image of the subject. The machine can be a rapid prototyping machine.

BRIEF DESCRIPTION OF THE DRAWINGS

FIG. 8 along with steps described herein may be used to determine whether a point on the surface of the subject that is contacted by the article upon attachment is a "non-opposing point" as defined herein.

DETAILED DESCRIPTION

The invention provides devices and methods for a wide range of medical diagnostic and therapeutic procedures guided by a customized subject-specific article that can be applied to a surface of a subject in a spatially unambiguous manner. The article, when applied on the surface of the subject, serves as an external reference for precise alignment of a medical procedure such as a biopsy or radiation beam along a unique trajectory. Thus, the invention enables a clinician to accurately guide a medical procedure along a preplanned route to reach an internal target in the subject, such as a brain tumor, without the need for conventional tracking technologies. Embodiments of the subject-specific contoured article can incorporate various features specific to the particular operation, such as a custom-angled probe guide for a biopsy, surfaces to attach skin retraction clips, structures for attachment of fixtures used to perform specific portions of the operation, or external reference markers for aligning a radiation source along a preplanned trajectory.

The inventive method generally begins by obtaining or acquiring a 3-dimensional image of the subject's anatomy proximate to a target region, for example the head of a patient with a cranial tumor. Generally, a computer generates a 3-dimensional dataset using techniques well known in the art, from a series of 2-dimensional images provided by a typical medical imaging device, such as a CT or MRI scanner. However, in certain cases, a single 2-dimensional image may be sufficient.

Figure 2:
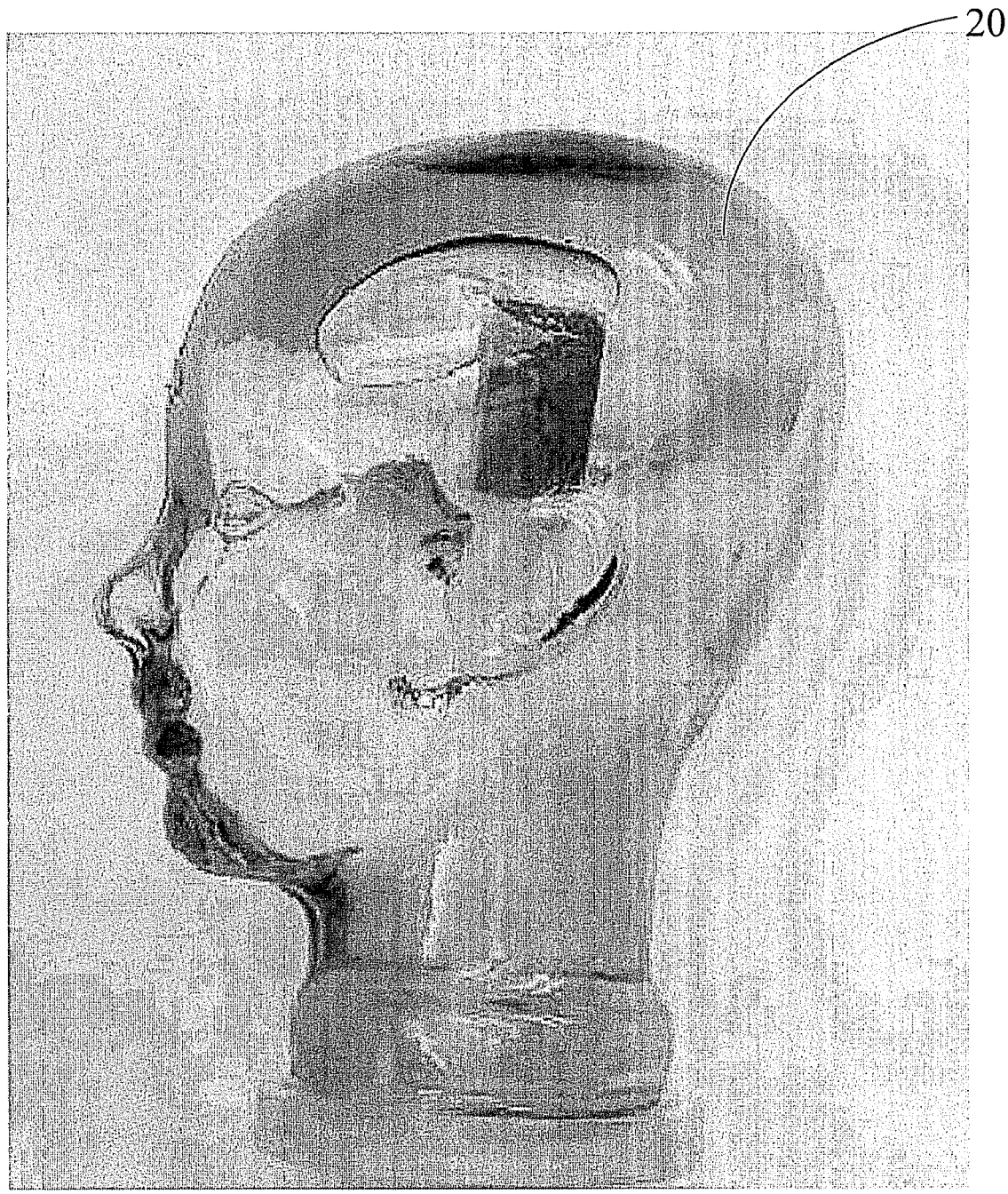
FIG. 2 is a scanned photograph of glass model of a human head used for CT scanning and 3-dimensional modeling.

In contrast to previous approaches which generally use external frames attached using bone anchors or fiducial markers applied to the subject as spatial references, the invention utilizes the contours of the subject-specific reference contour of the article, which replicate the surface contours of the subject itself. As an example, FIG. 2 shows a prior art 3-dimensional glass model of a human head 20 which was scanned by CT. As shown below, the data therefrom can be used to fabricate an article that uniquely fits on the glass model 20. The glass model 20 shown in FIG. 2, or any other tangible model of the subject, is not required to practice the invention.

The contours of the subject's surface in a computer-generated virtual model are then used to generate a virtual subject-specific article that conforms precisely to selected surfaces of the virtual model. In the example shown in FIGS. 3A and 3B and described in further detail below, a computer was programmed to design a T-shaped arc-like article 100 conforming to contours of the virtual head 110, fitting from ear to ear along a coronal plane, and projecting forward along the mid-sagittal plane, to include the eyebrow ridge and nose. The spatial coordinates of the virtual subject-specific article were then used, inter alia, to direct the fabrication of an actual subject-specific article having dimensions following or conforming to the patient's surface contours. As noted above, and described in further detail below, the article is subsequently applied to the subject prior to beginning the medical procedure and used for guiding the procedure to a particular location and optionally along a chosen trajectory, and/or to practice therapeutic approaches in any desired plane of view.

As shown in FIG. 3B, the inventive device upon attachment resides exclusively on the front of the head. As used herein, the "front of a head" is the portion of the head that includes surfaces of the head anterior to a coronal plane passing through the head approximately 1 inch posterior to the mid-coronal plane. In general, the front of a head does not include the occipital region. In particular, the front of a head does not include the portion of the head that contacts the scanner table when a subject is in the supine position.

Since the present invention is applied to the front of a head it may be applied and removed during surgery without removing the head from the head holder, such as a Mayfield device, used for neurosurgery and similar procedures. This makes the invention particularly useful for multistage surgeries where it may be desirable to perform certain procedures with the subject-specific article and others without it. Proper attachment of the device during surgery may be aided by including a structure for attachment of a stereotactic phantom device. The stereotactic phantom device allows the surgeon to confirm that the alignment of the device is proper for the preplanned medical procedure before proceeding with the procedure on the subject.

Stereotactic biopsy has long relied upon phantom testing to ensure the accuracy and precision of biopsy frame setting. The steps in the phantom procedure are generally as follows:
1) analyze various 3D scan data and select the optimal target and entry coordinates;
2) calculate a trajectory and setting for a stereotactic frame;
3) adjust the stereotactic biopsy frame to the calculated settings;
4) set the phantom base with a ring that matches the ring applied to the patient to the target coordinates;
5) set the stereotactic biopsy frame onto the phantom base;
6) adjust the biopsy probe to the required length;
7) inset the biopsy probe into the stereotactic biopsy frame applied to the phantom base; and
8) ensure the tip of the biopsy needle touches the phantom target point.

The above described procedure ensures that the stereotactic biopsy frame is correctly set and that once it is placed on the patient it will in fact target the correct tissues. For patient specific reference frames fabricated using rapid prototyping technologies according to the invention it is desirable to provide a similar procedure. However, there is the issue of the patient specific frame not having any fixed reference geometry, but instead having a geometry to uniquely fit the patient's anatomy. It was concluded that the phantom test is a valuable portion of the existing procedure and that there is significant value to providing a similar test for surgeons prior to using the frame for patient application.

The above problem with patient specific frames can be overcome by an inventive design that incorporates external references, such as sockets on the patient specific mask. These reference sockets are placed at known coordinates. The phantom base is adapted to also contain mating portion of these sockets. Knowing the phantom base coordinates and the patient specific mask coordinates allows calculation of the required setting of the phantom target. Accordingly, a parallel test to that employed on the patient can be performed prior using the frame for the procedure on the patient.

To allow for translation of the preplanned settings of the relevant medical tools, such as the entry point and angle of a biopsy probe or a radiation beam, from the "virtual operating room" to the real world, the operation may be visualized in a computer. For example, an appropriate angle for a trajectory may be planned to avoid contacting or penetrating certain anatomical features, such as a large vein.

Once a selected entry point and trajectory for the medical procedure is determined, information necessary for frameless guidance of the actual medical procedure can be directly incorporated into the design of the fabricated patient-specific article. A stereotactic workstation is preferably used for planning the trajectory of a surgical approach, biopsy or radiation procedure, for practicing the approach in virtual space, and for designing and directing the fabrication of the subject-specific article(s).

Figure 4:
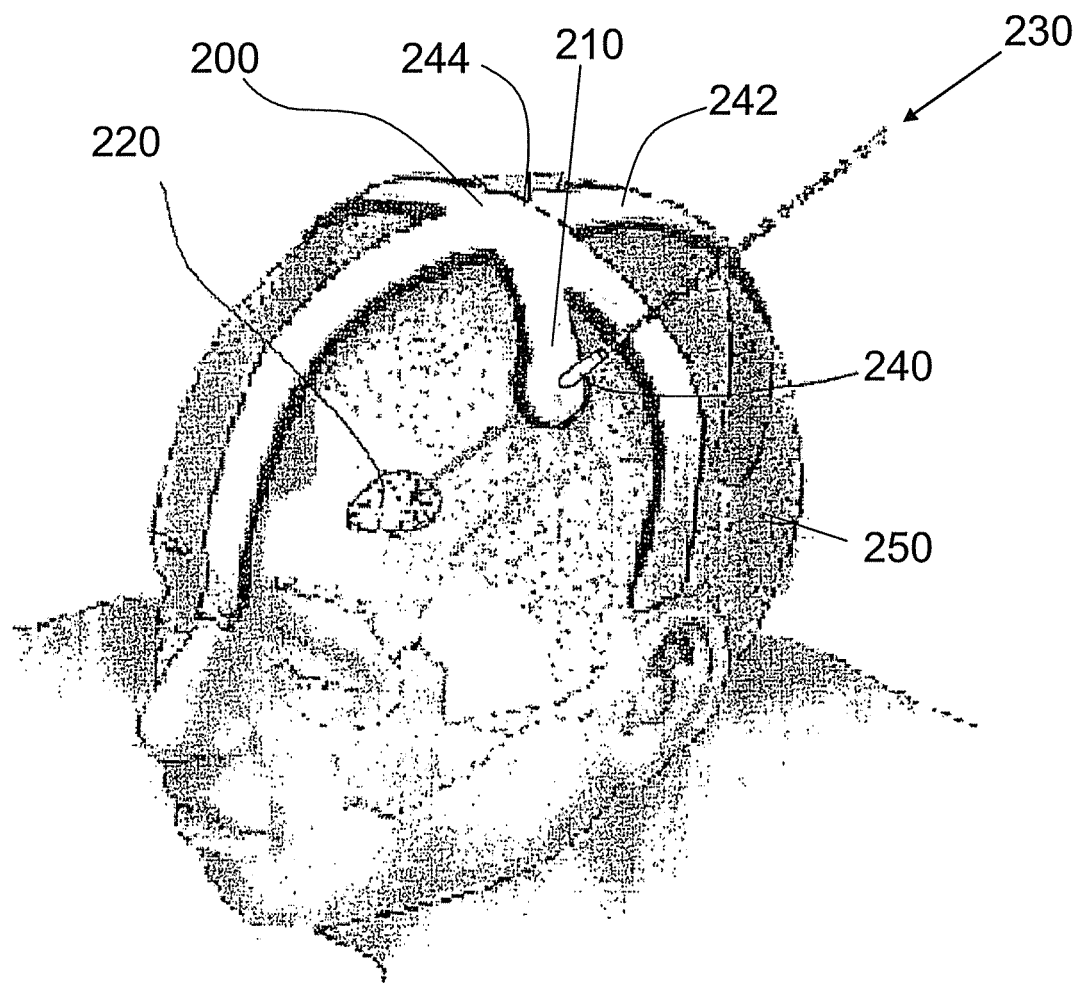
FIG. 4 is a drawing of a subject with an intracranial tumor fitted with a subject-specific article that fits directly on the skin surface. The article includes a probe guide, according to an embodiment of the invention.

As an example, FIG. 4 illustrates a shaved patient fitted with a customized article 200 that includes a portion 210 that overlies a known location of a tumor 220 in the patient's brain along a planned trajectory for the procedure 230. In the case of a biopsy procedure, following removal of a section of the skull, such as by making a burrhole, a biopsy probe (not shown) can be inserted into the brain at the predetermined angle 230 that is guided by a biopsy probe guide 240 fabricated into the article 200. The angle 230 need not be normal to the surface of the article 200, but rather can be any angle appropriate for directing the insertion of the probe along the selected trajectory. In the embodiment of the article 200 shown in FIG. 4, the biopsy probe guide 240 comprises a rigid channel protruding from the plane of the article 200 and extending to the surface of the patient through an opening (not shown) in the article 200.

FIG. 4 is used to illustrate how a portion 210 that overlies a known location of a tumor 220 and a biopsy probe guide 240 may be incorporated into an article of the present invention. As shown in FIG. 4, the article 200 includes a portion that project toward the anterior portion of the head 242. For purposes of the present invention, this portion 242 could be removed along the dotted line 244. After removing portion 242 at line 244, the device in FIG. 4 resides exclusively on a front of a head.

The article 200 can further include a structure (not shown) for directing an incision or biopsy depth attached to the article 200. The required depth of penetration of the surgical tool, such as a biopsy probe, is pre-calculated during the computer-assisted planning of the procedure, and is related to the known geometry of the probe guide 240 and the article 200. During the medical operative procedure, the depth of probe insertion can be controlled by various means, for example, by using an adjustable stopping mechanism on the biopsy probe (not shown), positioned to come to rest against the external opening of the probe guide 240 when the biopsy probe tip is advanced to the desired depth for sampling the tissue of interest. The depth of the biopsy, being controlled by a stopping mechanism, can be set by measurement, for example using a ruler. Alternatively, a custom fabricated guide holder (not shown) can include a probe setting guide, such as a ridge or other indicator, at the appropriate position for setting the stop on the biopsy probe. The custom use probe setting guide holder, being specific for the operation, can advantageously provide the user with a no-adjustment guide to accurately set the position of the stop, and hence the length of the biopsy needle to be inserted.

In one embodiment, the probe guide 240 can be designed to be integral to the device and thereby fabricated as an extension of the article 200 having the appropriate angle to direct the insertion of the biopsy probe. Alternatively, the device can be made with an opening (not shown), such as a square hole of standardized dimensions, at an appropriate site on the contoured surface. In the use of embodiments having such openings, a separately fabricated custom-angled probe guide having a base that fits the standardized opening can be inserted into the hole in the device and secured in place, for example by a screw. In some cases this separate piece may be used as a further attachment site for other components (not shown), such as a stainless steel chuck used to guide the biopsy needle or a stereotactic phantom device.

An adjustable fit can be provided by the article, such as by adding fasteners to the article 200. For example, adjustability of the fit of a custom article can advantageously allow for the presence of hair or other surface features on a patient's head, and for repeated use of an article on the same patient whose surface features (such as hair length) may change from time to time. As an example, the article 200 illustrated in FIG. 4 was designed to be applied to a smooth hairless surface 250. However, in routine clinical applications, the entire surface required to seat the article is generally not smooth and hair-free. Rather, it is now common practice to perform cranial surgery without shaving all or even a portion of a patient's hair. Instead, the scalp is scrubbed with sterilizing solution and the hair is parted along the path to accommodate a skin incision. Accordingly, in some instances it is anticipated that the design for contact between the skin and the article will be required to accommodate for the presence of hair.

Figure 5:
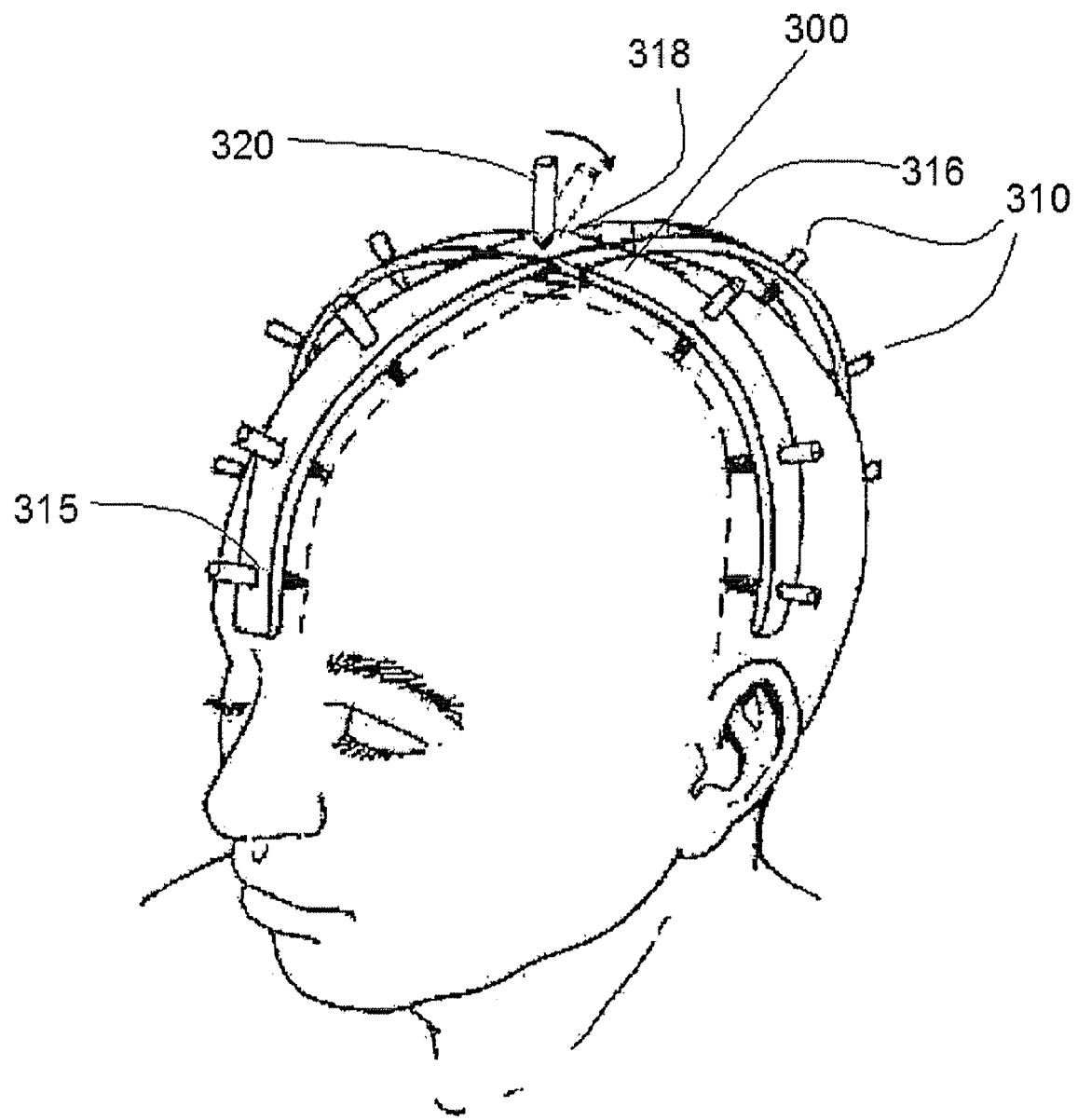
FIG. 5 shows a device including an article and adjustable fasteners that rest on the surface of the scalp, providing clearance for hair, and including an adjustable probe guide, according to an embodiment of the invention.

FIG. 5 illustrates an embodiment of an adjustable-fit custom article 300 that includes a plurality of adjustable fasteners 310 that can have their length beyond the surface of the article 300 be adjusted. For example, when the fasteners 310 are lengthened as shown in FIG. 5, the article position adjusted by the fasteners 310 will be moved outward from the scalp. The article design can include instructions to fabricate such adjustable fasteners 310 from any suitable material, such as epoxy. The software preferably enables the fasteners 310, and corresponding openings 315 in the article 300 to accommodate and allow for adjustment of the fasteners 310, to be automatically applied to the custom article 300 wherever designated by the user.

As shown in FIG. 5, the article 300 includes a portion that project toward the anterior portion of the head 316. For purposes of the present invention, this portion 316 could be removed along the solid line 318. After removing portion 316 at line 318, the device in FIG. 5 resides exclusively on a front of a head.

From the standpoint of fabrication, the feature of adjustability may permit greater flexibility and economy if the final product can be adjusted for ideal fit after placement on the patient. Although current equipment is capable of fabricating an entire subject-specific custom article in a time that is compatible with the current planning process for the medical procedure, it may be desirable to include as much standardization into the design as possible, and in some cases to apply generic designs or masks for article design.

Some embodiments of the adjustable-fit articles such as the article 300 may include separate stereotactic phantom devices or probe guides, as described above, that are not integral to the mold for the article 300. Referring to FIG. 5, the base of a probe guide 320, or stereotactic phantom device (not shown), can be secured to the opening of the article 300 in a fashion that allows it to be adjustable in three dimensions, permitting minor adjustments of the angle of the probe guide following fitting of the adjustable-fit article on the subject's head. The ability to make such adjustments to the probe guide 320 allows the user to compensate for positional changes made during the adjustment of the article 300 on the subject's surface. The ability to achieve alignment using a stereotactic phantom device allows the user to adjust the device until alignment of the article matches the designed alignment.

The computer code for frameless stereotactic procedure planning can be built on user interfaces and algorithms known in the art that have been successfully used in a current frame-based program. The required infrastructure regarding image transfer, DICOM receivers, and mass storage can be accommodated by the imaging infrastructure contained in this software. A unique feature of the code used in the invention is the ability to direct the fabrication of a tangible structure, such as a subject-specific article, based on the coordinates of a computer-generated three-dimensional model of a portion of a subject.

The basic graphical user interface for biopsy targeting and trajectory selection is generally built around the reformatting of multiple 2-dimensional diagnostic images from a CT or MRI dataset into orthogonal and oblique views, as well as solid renderings of the 3-dimensional database. Existing frame-based biopsy programs rely upon a system centered around a rigid frame-based stereotactic arc, i.e., CRW (Radionics, Mass.) for this purpose. This mechanical system requires the setting of multiple biopsy-specific coordinates and angles. In contrast, the workstation interface used to implement the invention incorporates all of the required patient-specific guidance alignment directly into a patient-specific article, such as the article 200 shown in FIG. 4. For biopsy procedures, a biopsy probe guide 240, as described above, can be fabricated based on the known geometry of the target tissue site relative to the contoured article.

In contrast to previous frameless approaches, neither special fiducials nor bone anchors need to be applied to the subject prior to diagnostic imaging by CT or MRI scanning. The only scanning criteria are that plane pixel dimensions generally be less than 0.75 mm, and slice thickness be equal to or less than 1.0 mm. These parameters are used to set a minimum spatial resolution of the input diagnostic dataset. As used in other techniques for frameless image guidance, scanner coordinates are used for mapping the scan into pseudo-stereotactic space. Early CT scanners required fiducial systems to ensure accurate knowledge of gantry angle and table position. However, modern scanners are equipped with high-resolution gantry and table position sensors, making external fiducial systems unnecessary. Much of the data provided by modern multi-slice scanners is generated through post-processing of raw scan data. State-of-the-art scanners are also equipped to obtain CT data using helical scanning techniques.

To confirm the accuracy of scans without fiducial markers, a radiosurgery database compiled from a large clinical practice was queried to document the extent to which either gantry angle or table index required a frame-based system to correct for scanner reported position by more than 1 voxel, i.e., by more than 0.75 millimeters in plane or 1 millimeter out of plane. No errors requiring a software correction of greater than 1 voxel were detected in 100 frame-based stereotactic scans.

Figure 1:
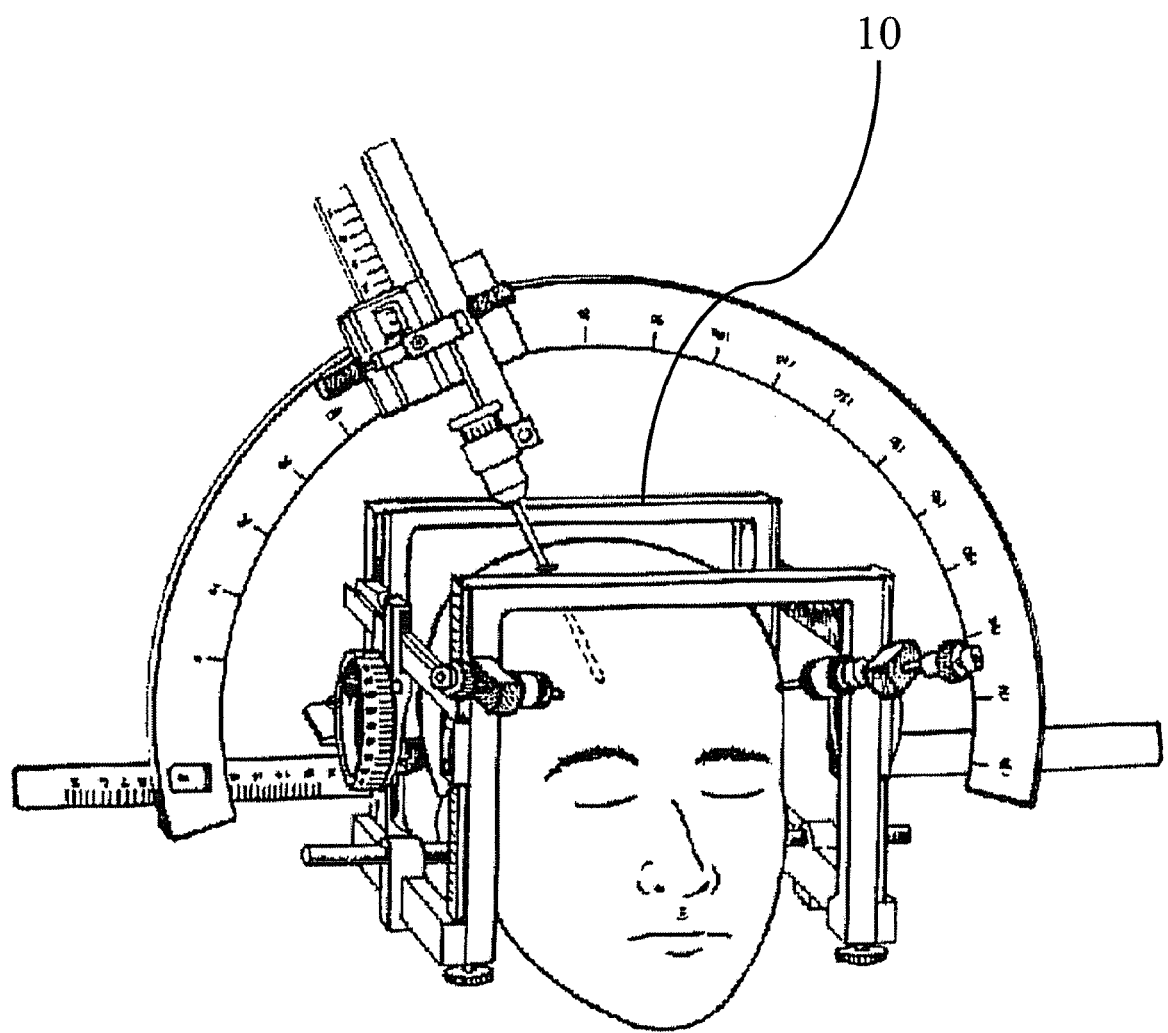
FIG. 1 is a drawing of a patient wearing a prior art head frame used for stereotactic neurological procedures.

Subject-specific articles for guidance of medical procedures according to the invention have the advantage of not requiring the imaged voxel to be mapped to a rigid stereotactic reference frame, such as that shown in FIG. 1. As discussed above, the approach creates a self-contained reference system based on the subject's specific surface article, such as that of skin or other anatomical landmarks such as bony structures. Since the position of the subject in the scan volume does not affect the resolution of the 3-dimensional subject-specific model, the subject-specific article technology does not impose any special scanner-subject alignment criteria.

CT and MRI datasets are presented to the system as individual voxels, each with an associated 3-dimensional coordinate. These discrete data elements are coupled to the design of the subject's custom article. For biopsy procedures, the article is preferably in turn coupled to the geometry of a biopsy probe guide, such as probe guide 240. When dealing with such coupled datasets, the algorithms are carefully controlled so as not to lose spatial accuracy through successive processing of the input data.

The alignment of the patient 3-dimensional dataset and the custom article dataset is further affected by the need to align the custom article to a device for fabrication. Any suitable fabrication method and materials, and any machine capable of forming a device from a computer-generated design, such as computer-controlled cutting or milling equipment, can be used, and more preferably those providing products most quickly and economically. The subject-specific devices and articles are preferably fabricated using rapid prototyping. Any rapid prototyping fabrication method suitable for the purpose may be used. Rapid prototyping devices generally use a standard interface language for data input, such as Standard Triangulated Language or STL. An STL file consists of a series of triangle facets describing a closed 3-dimensional shape. Each facet is described by a 3-point 3-dimensional coordinate, and a direction indicating whether the surface is facing in or out. The spatial resolution, or spatial fidelity, of the final object is a product of the number of STL-defined vertices, or facets, and the resolution of the rapid prototyping process. A specific example of the use of an STL file to design and describe a custom article suitable for fabrication by rapid prototyping is further described below.

The most straightforward method to produce a high fidelity subject-specific article entails using a very large number of triangles to maximize spatial resolution. In the operating room setting however, this may be impractical because the number of vertex points must be balanced against the speed of rendering and size of the imported 3-dimensional diagnostic dataset. Speed of fabrication may be an issue where it is desirable to be able to rapidly fabricate the article shortly after the scanning process is complete, permitting performance of the medical procedure on the same day, and ideally within hours, of performing the diagnostic scan.

Maximizing the resolution of the subject-specific custom article while minimizing the number of vertex points used to describe the article requires that special attention be paid to the orientation and position of the custom article, and especially the biopsy guide, in the STL file coordinate system. Several approaches may be used for this purpose.

One solution is to design the biopsy probe guide as a generic high-resolution object and merge this object to the prescribed biopsy trajectory. Another approach is to fix the position of the biopsy probe holder relative to the STL coordinate system. While the user views the patient as stationary in the planning system's orthogonal windows and the target position and biopsy trajectory as variable, the custom article and trajectory are kept aligned to the STL grid while the orientation of the patient model is adjusted. These matrix manipulations are similar to ones applied in previous systems, such as in codes previously written for radiosurgery, stereotactic frame-based biopsies, atlas mapping for deep brain stimulation, frameless radiosurgery code and 3-dimensional ultrasound.

In one embodiment, a basic design criterion of the system can make the user interface and the underlying computation code platform independent. Other designs are possible. As described in further detail in the example below, a demonstration code was entirely written in VTK to provide such portability. The code used for this purpose resided on a Linux workstation planning computer. To provide the ability to plan a case and design the required article and custom components remote to the planning computer, a secure web-based interface can be provided to accommodate such access.

The above analysis of surface model accuracy is coupled with a custom mold design algorithm to provide the user with guidance as to which portion of the subject's surface will result in the most accurate alignment of a custom fabricated article to the subject at the time of surgery. For example, when a subject is in the supine position, the pressure of the head on the scanner table or head holder makes it difficult to accurately image the occipital region. Therefore the algorithm is written to provide the surgeon with the option to choose from several cranial surfaces for reference. A selection of frame masks, i.e., geometric contour designs, is presented to the user, allowing for rapid evaluation and optimization of article alignment and geometry for each individual clinical case.

Since the inventive article resides on the front of a head, the present invention avoids the fit problems inherent in articles that reside over the occipital region upon attachment. Furthermore, the fit of articles that reside over the occipital region is impaired because of the pressure exerted during surgery by the head on the surgical table. Another benefit of the present frameless article is that it may be designed so that it can be removed or attached without interfering with the use of common patient immobilizers, such as the Mayfield device, which is presently the most common method of patient immobilization for cranial surgery.

Article designs can be customized to include surgical site markers, custom skin clips and retractors. During a neurosurgical procedure, it is common for multiple structures to be successively added to the operative field in order to hold skin flaps and retractors, such as Greenberg or Yasargil retractor systems. When the subject-specific article is planned at the stereotactic workstation, the design can include not only all of the information usually provided during frameless image guidance, but also features providing instructions for guiding surgical procedures, in some cases at successive stages in the procedure.

Figure 6:
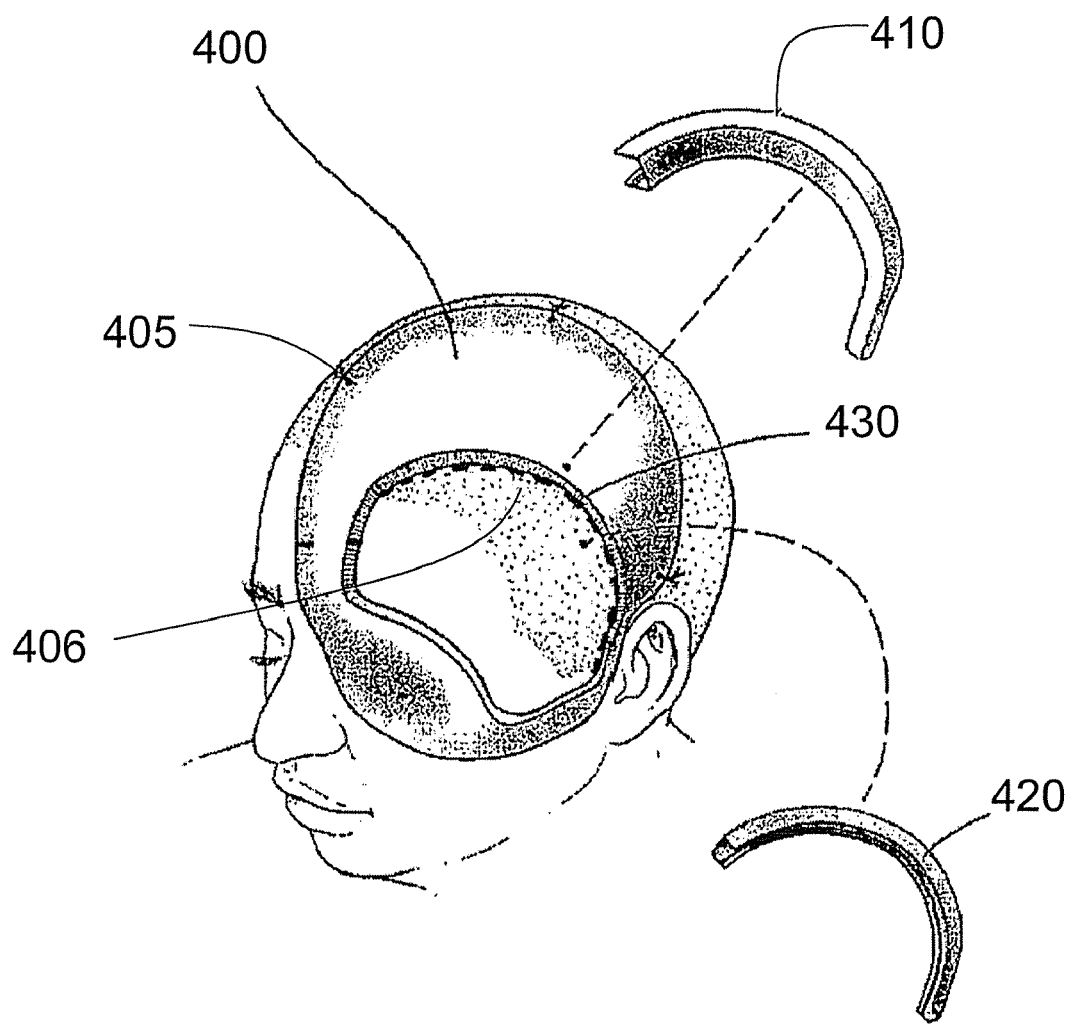
FIG. 6A shows a device including a subject-specific article in three sections. The first section fits and aligns to the subject's surface, establishing the initial reference and providing attachment for the other two sections, each comprising a custom skin clip, according to an embodiment of the invention.
FIG. 6B shows the custom article of FIG. 6A with a skin flap retracted after incision, and held with a custom skin clip, according to an embodiment of the invention. Skin clips are applied to the edges of the incision to control bleeding.
Figure 6:
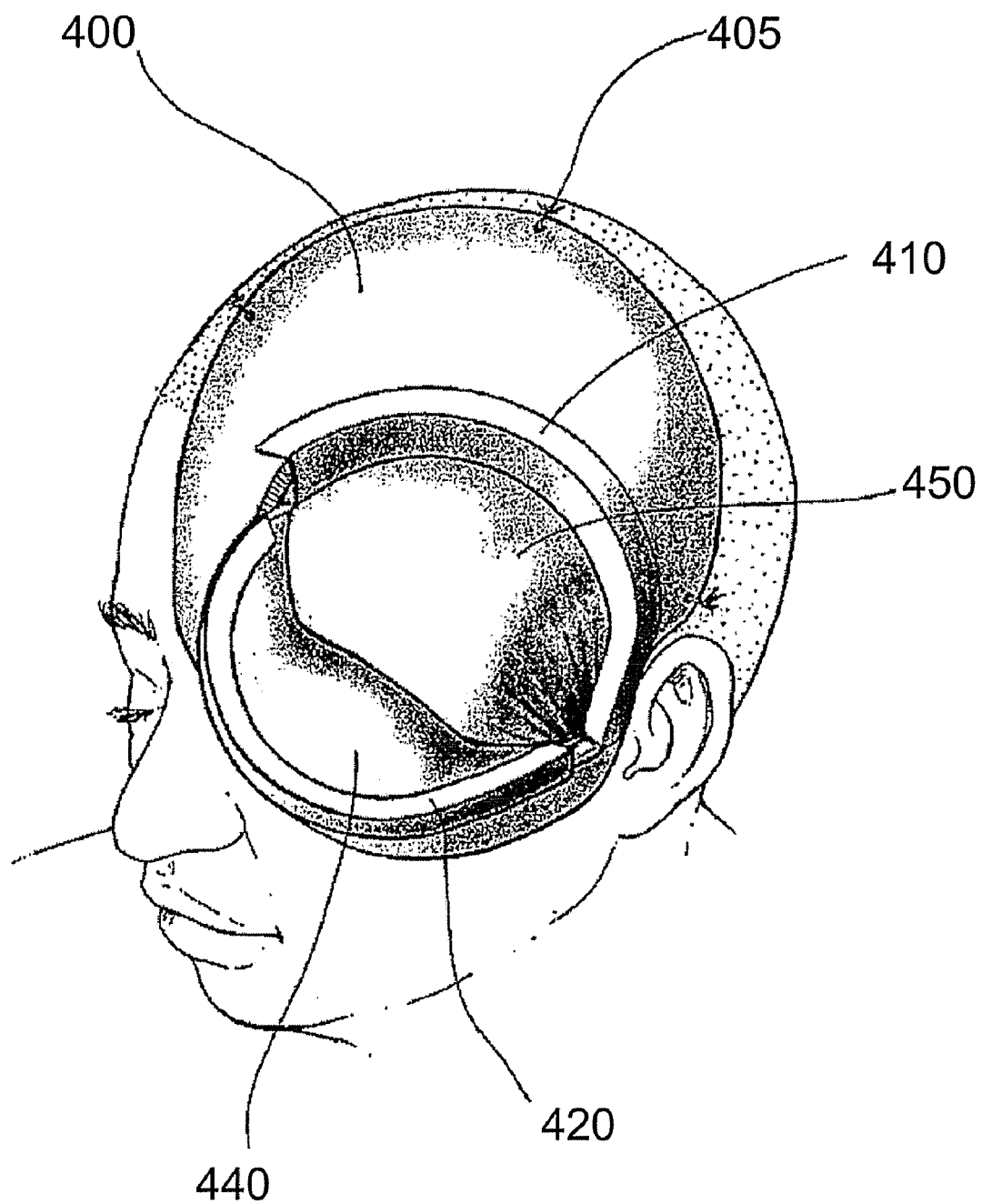

For example, the article can include one or more cutaway portions aligned along a preplanned site for a skin flap, craniotomy or craniectomy. Along with this information, custom skin clips and retractors can also be planned and incorporated into the design of the custom article. FIG. 6A illustrates an example of an article 400 including surfaces 406 for attachment of custom skin clips 410 and 420. In the figure shown, the head of the patient is shaved, and the article 400 is secured to the patient's head using exogenous fasteners, such as surgical sutures 405. Any other type of suitable fastener can be used, such as velcro strips positioned on the article 400 so as to be attachable to a velcro head harness worn by the patient. In an embodiment of the invention, exogenous fasteners, such as surgical sutures 405, are not used. As shown, the custom article 400 as attached exclusively resides on the front of a head.

In the practice of using a custom article such as article 400, a surgeon first makes an incision through the scalp along a preplanned course 430 (dotted lines) using a cutout edge of the article 400 as a guide. In the next step, shown in FIG. 6B, the skin flap 440 is then retracted, and stabilized using the custom skin clips 410 and 420 that are fabricated to fit over the contours of the cut edges of skin and to be secured to the article 400 as shown in FIG. 6B. Application of the skin clips 410 and 420 along the cut edges of the skin advantageously limits the bleeding of the skin effectively and rapidly.

To further guide the procedure at successive stages, additional custom-designed attachments can be secured to the article 400 and used in a stepwise fashion. For example, a stereotactic phantom device (not shown) to insure proper attachment of the article or a guide (not shown) may be secured to the article 400 that marks the borders or site of removal of the bone from the skull. For the subject depicted in FIG. 6B, a portion of the skull has been removed and the underlying exposed portion of the brain 450 is seen. The next step in the surgical operation on the exposed brain 450 of the subject may be to perform a deep incision along a preplanned trajectory to reach an embedded tumor. To assist in the placement of the incision, another customized attachment (not shown) could be secured to the device 400, for example by one or more screws that would provide further instructions for localizing the surgical site. In this way, directions are provided by the attachments for multi-level guidance of the procedure.

Some embodiments of the subject-specific article can be advantageously used for radiosurgery. Referring again to FIG. 1, prior art stereotactic procedures for high precision neurosurgery and radiosurgery can require the use of a rigid head frame 10 which is attached to the head of a patient. Because the position of the target within the patient's head is known relative to the rigid frame 10, the radiation beam can be guided to a target location with a high level of precision. In contrast, embodiments of subject-specific article of the invention for use in high precision radiosurgery eliminate the need for a rigid head frame such as shown in FIG. 1, thus reducing patient discomfort and other problems associated with head frames.

Figure 7:
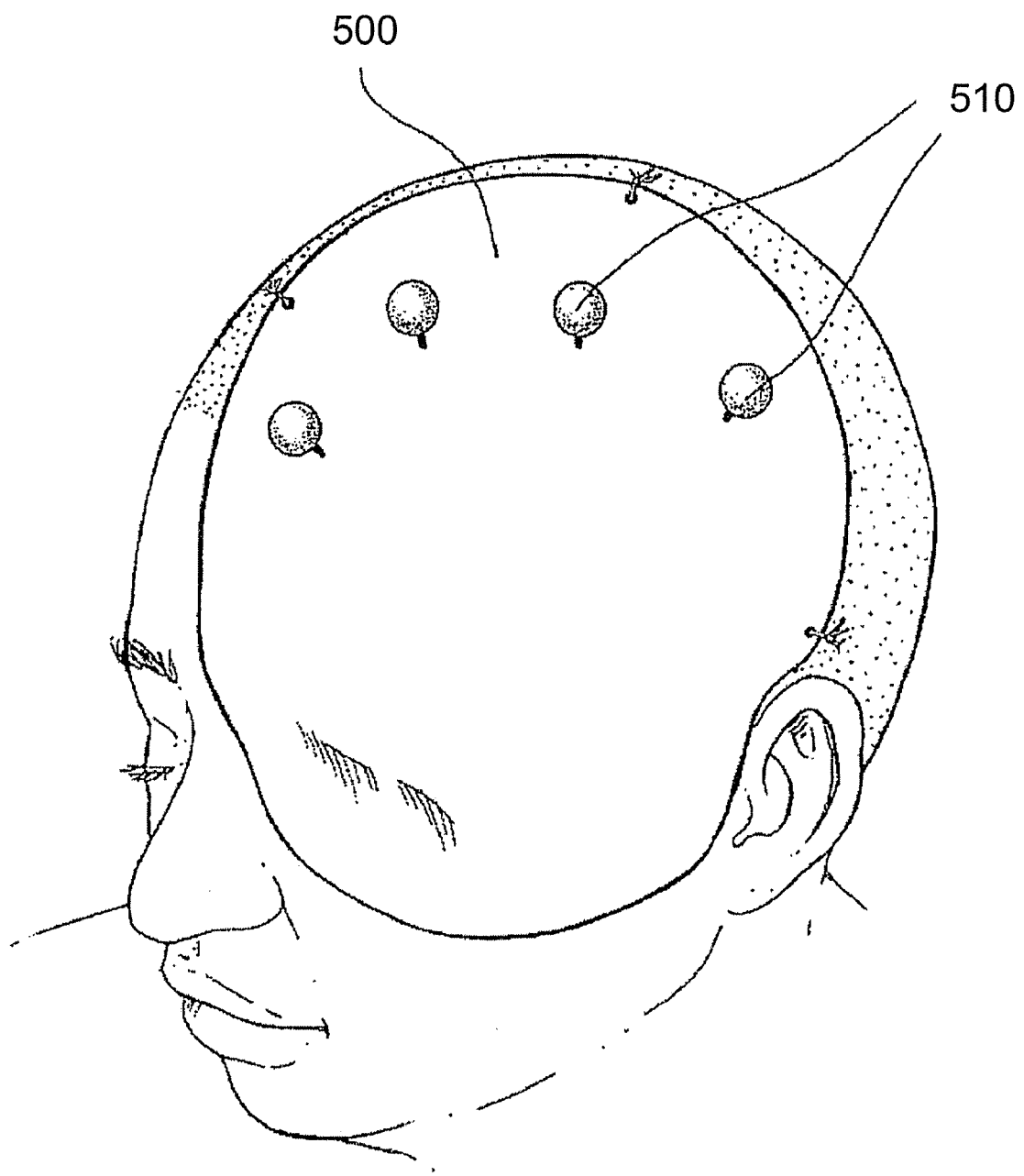
FIG. 7 is a drawing showing a subject-specific article including external reference markers, according to an embodiment of the invention.

FIG. 7 shows an embodiment of an article 500, which resides on the front of a head, used for radiotherapy procedures. With the knowledge of the geometry of the patient's surface, and of the position of the radiation beam relative to the subject-specific article 500, a radiation beam can be accurately aimed at the patient, its alignment calculated from the spatial coordinate information contained in the article 500. Aiming of the treatment beam can be accomplished in several ways. In one embodiment (not shown), a subject-specific device can be designed to mount onto a radiation source, such as a linear accelerator. In such embodiments, the device can include one or more fastening devices such as mounting screws typically used for attachment of head frames to linear accelerators.

Alternatively, as shown in FIG. 7, the article 500 can be fabricated to include external reference markers 510, such as optical markers, designed to be included with the article 500 for registration to the scalp of the patient. Any number and type of suitable reference markers 510 can be disposed upon or otherwise incorporated into the article 500. Markers 510 illustrated in FIG. 7 comprise part of a conventional optical image guidance system (other components not shown). Because the relative positions of the markers 510, the article 500, and anatomical structures within the patient are known, automatic registration between the patient and the radiotherapy treatment device can be achieved using an otherwise conventional optical image guidance system. Thus, the subject-specific article 500 provides a unique alignment between the known geometry of the markers 510 and the patient's scanned geometry.

Figure 8:
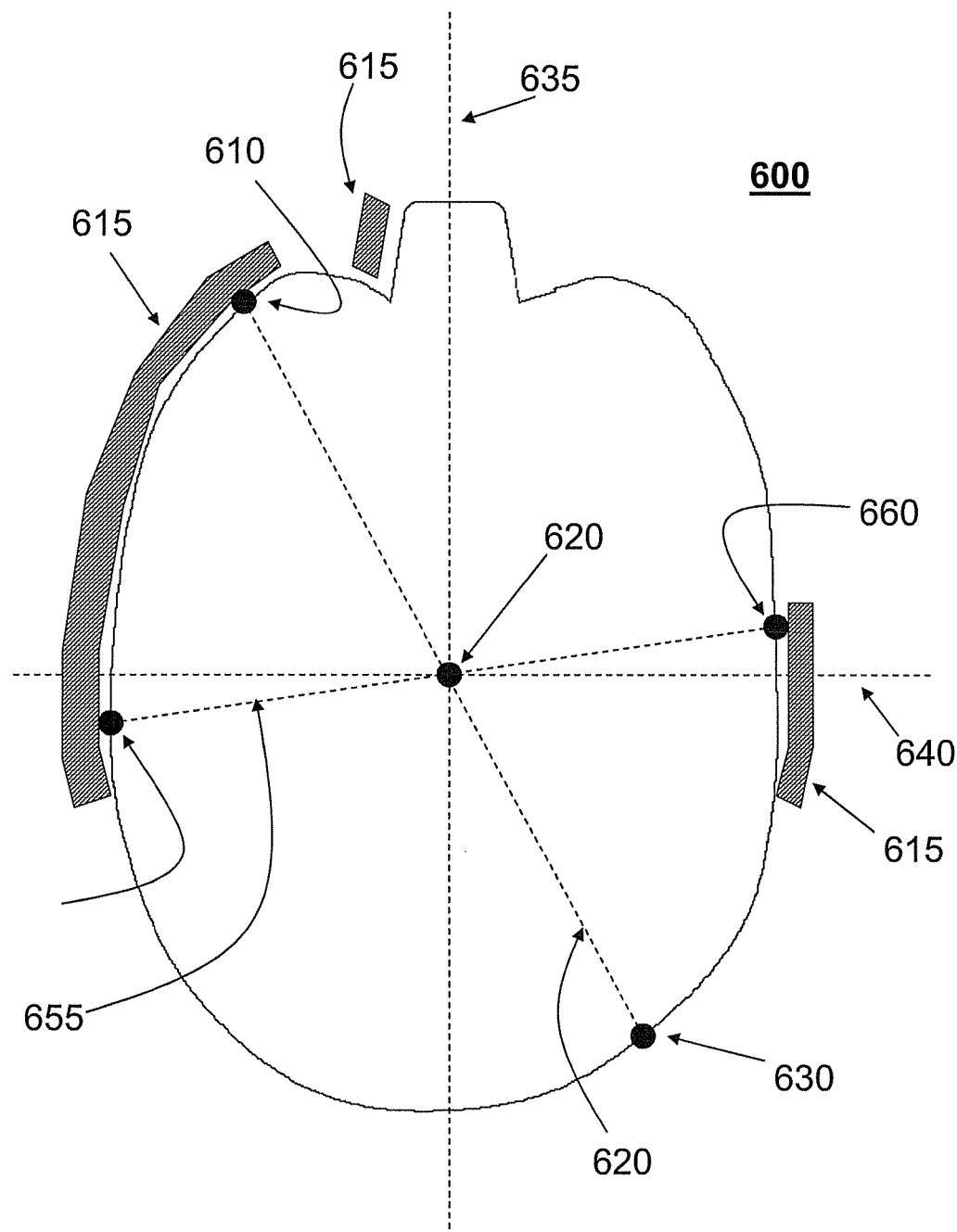
FIG. 8 is an axial cross-section of a head.

The articles 400 and 500 depicted in FIGS. 6A, 6B, and 7 are examples of articles that, upon attachment, exclusively contact non-opposing points. FIG. 8 along with the following steps may be used to determine whether a point on the surface of the subject that is contacted by the article upon attachment is a non-opposing point as defined herein. An axial cross-section 600 of the head is shown in FIG. 8. In a first example, point one 610 is a point that is contacted by the article 615 upon attachment to the head. To determine whether point 610 is a non-opposing point, a chord 620 is drawn starting at point one 610 that passes through the center of the head 625. Point two 630 is the end of the chord 620 on the side of the head opposite point one 610. If point two 630 is not contacted by the article 615 as attached, then point one 610 is a non-opposing point. If point two 630 is contacted by the article 615 as attached, then point one 610 is not a non-opposing point. In the first example, point two 630 does not contact the article as attached, so point one 610 is a non-opposing point. For purposes of this determination, a "point" may be a square with a side dimension of less than or equal to about 1 mm. For purposes of this determination, the center of the head 625 is the intersection of the mid-sagittal plane 635 and the mid-coronal plane 640.

In a second example, still referring to FIG. 8, another point one 650 may be selected. Drawing a chord 655 from point one 650 through the center of the head 625 reveals the location of point two 660. Since point two 660 of this example contacts the article 615 as attached, point one 650 is not a non-opposing point. Based on the foregoing, it should be clear that the articles 400 and 500 depicted in FIGS. 6A, 6B, and 7 are examples of articles that, upon attachment, exclusively contact non-opposing points.

As noted above, the subject-specific articles of the invention are preferably produced using rapid prototyping technology. Currently available rapid prototyping fabrication techniques include stereolithography, wide area inkjet, selective laser sintering, fused deposition modeling, single jet inkjet, three-dimensional printing and laminated object manufacturing. In each case, suitable materials are known in the art and based on the particular fabrication technology. Any suitable rapid fabrication method and materials can be used.

For application in a clinical or surgical setting, the articles must generally withstand routine rapid sterilization conditions. A pre-vacuum cycle that places the materials to be sterilized at about 270 degrees Fahrenheit for approximately four minutes or a suitable chemical sterilization procedure, such as provided by Steris systems (Mentor, Ohio), is generally utilized. While gas sterilization is possible, it is anticipated that the overnight cycle routinely required by this process would limit its applicability where a same-day fabrication process is either desired or necessary.

Of the above fabrication techniques, currently preferred choices for rapid prototyping in the medical operative environment include 3-dimensional printing (available from Z Corp., Burlington, Mass.) and fused deposition modeling (FDM) (Stratasys Corp., Eden Prairie, Minn.). Because manufacturers of rapid prototyping systems have generally standardized upon the STL protocol as input, newer machines and materials that may become available in the future can be used to upgrade the invention in a manner transparent to the end user.

As described in the example below, both of the above rapid prototyping systems were tested in the practice of the invention and found to produce acceptable articles. Both systems are capable of fabricating the required parts in less than one hour. The FDM technology provides an advantage in that upon completion of the building process, the part is ready for use. The 3-dimensional printing process is faster than FDM, but has the drawback that the produced article is relatively fragile and requires an epoxy resin bath to provide the required strength.

An exemplary 3-dimensional printing process involves successive application of layers of material. A layer of powdered material is applied to the fabrication bed, then the print heads apply an adhesive to bond devices together. The next pass applies another layer of powder that is again selectively hardened by the print head's application of a hardening substance. Because each layer of fabrication has a powder layer below, the fabricated part is self-supporting. The 3D printing system also provides the advantage of capability to fabricate parts in color, which may present an advantage in assembly of an article in the setting of a surgical operating room.

The FDM process builds each component by applying a thin layer of melted material at the required location. The fabrication process requires that parts with sloping surfaces use a "filler" material for support while the material is applied. This filler is automatically configured by the equipment and available in water-soluble varieties. A simple water bath is all that is required to remove the filler after fabrication.

Other types of materials besides those used for rapid fabrication may be used to fabricate the subject-specific articles and devices and are within the scope of the invention. In some applications, it may be desirable to fabricate the devices using malleable or otherwise recyclable materials suitable for repeated uses.

EXAMPLE

The following example serves to illustrate the invention without limiting it thereby. It will be understood that variations and modifications can be made without departing from the spirit and scope of the invention.

Example

Rapid Prototyping of Subject-specific Custom Article

The ability to create a reference contour from a medical image database requires that the medical image data set contain information sufficient to derive at least one or more contours of the subject's anatomy. The contour(s) are used to form an unambiguous spatial reference allowing the real world and the virtual world to be properly aligned. The uniquely fitting contour(s) can in turn allow a vector to be planned and projected to a specific targeted tissue region. In some instances it may be necessary to provide a full 3-dimensional description of the anatomic region involved, such as the head of a patient, while in other instances it may only require a single individual planar CT or MRI image. For example, it may be possible to designate a sagittal contour of the patient as the reference plane and to orient a biopsy vector using only that single plane. With the knowledge that the article is to be fitted to the sagittal plane, it may then be possible to accurately align a device with the sagittal plane so that the trajectory can easily be followed. In other instances, a more detailed 3-dimensional description of the patient's surface may be necessary to create the required article and an oblique trajectory.

For either a single plane or 3-dimensional surface, it is important to be able to create an article that can be unambiguously applied and rigidly attached to the subject. It is the unambiguous spatial fit of the article to the subject, as well as the known relationship of at least one reference contour of the article to the subject's anatomy, that provides the clinician with the information required to follow the preplanned trajectory.

To demonstrate the ability to begin with a series of 2-dimensional diagnostic images and to develop a subject-specific article, a code was written on a Linux workstation using the VTK (version 4.0) visualization tool kit. Referring again to FIG. 2, a 3-dimensional prior art glass head model 20 was scanned using a Siemens Somatom Sensation 16 CT scanner. For the scan, typical clinical settings were used (512×512 image matrix; 23 cm field of view; 0.75 mm slice thickness at 0.75 mm intervals). The initial datasets were transferred from the radiology Picture Archiving And Communication Systems (PACS), and the sequential CT slices were assembled into a volume dataset. For easy manipulation within the VTK environment, the dataset was interpolated onto a 0.5×0.5×0.5 millimeter data matrix. Using the VTK libraries, code was developed to threshold the scanned model head and to create a rendered surface.

Figure 3:
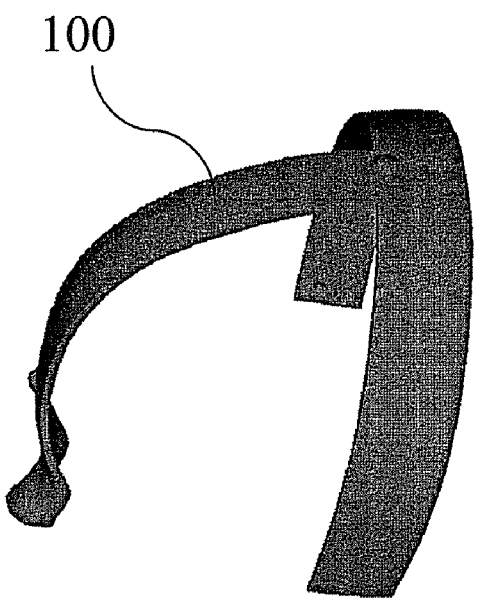
FIG. 3A is a computer-generated rendering of a custom article designed to fit the glass head model shown in FIG. 2, according to an embodiment of the invention.
FIG. 3B shows a computer rendering of the article shown in FIG. 3A positioned on the head model shown in FIG. 2, according to an embodiment of the invention.
Figure 3:
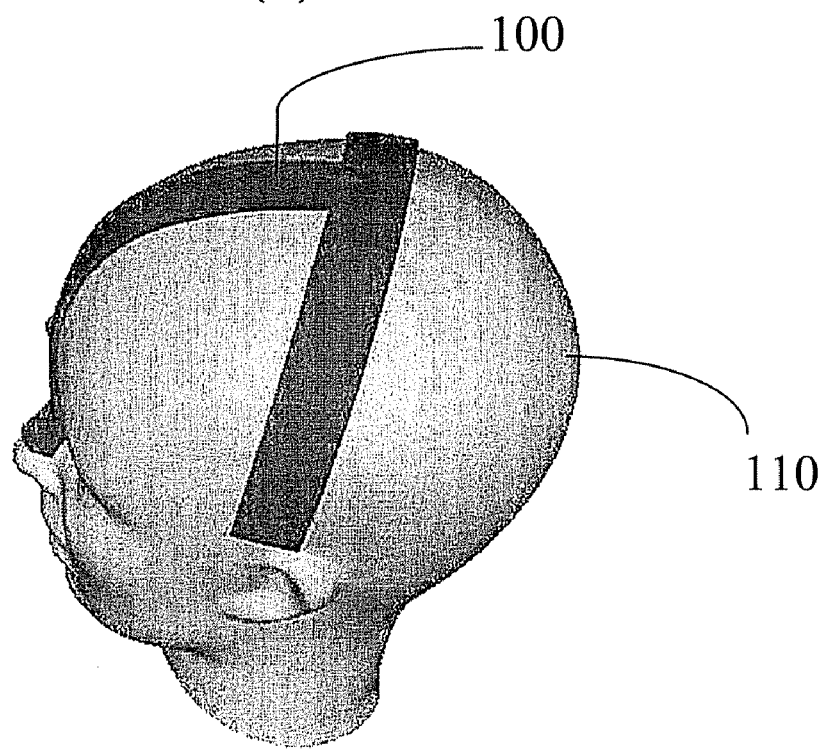

Referring to FIG. 3, to produce a custom shell of the scanned model, the rendered surface was then extended and the initial surface subtracted from the new volume. A mask was then used to operate upon the custom shell. The mask cut the shell so that a high spatial frequency surface, i.e., the mid-sagittal plane, as well as an orthogonal surface, i.e., the mid coronal plane, remained, and the rest of the shell was eliminated. The resulting article was designed to be approximately 2 mm in thickness and 2.5 cm wide. The width of 2.5 cm was selected to allow sufficient surface area to provide a unique fit. The thickness of 2 mm was selected to minimize fabrication time and cost, while maintaining sufficient rigidity. FIG. 3A shows a computer rendering of the article 100. FIG. 3B illustrates a computer rendering of the scanned head model 110, fitted with the custom article 100.

The VTK library was then used to write a description of this subject-specific article in STL format. Approximately 50,000 polygons were used to describe the article. The file describing the custom article was sent to two different rapid prototyping manufacturers for fabrication. The rapid prototyping technologies were selected based upon user cost, prototype accuracy and speed of fabrication. The techniques of stereolithography (3D Systems, Ann Arbor, Mich.), and three dimensional printing (Z Corp., Burlington, Mass.) were chosen for the test. Finished products were applied to the glass head model 20 shown in FIG. 2, and analyzed for fit.

Figure 9:
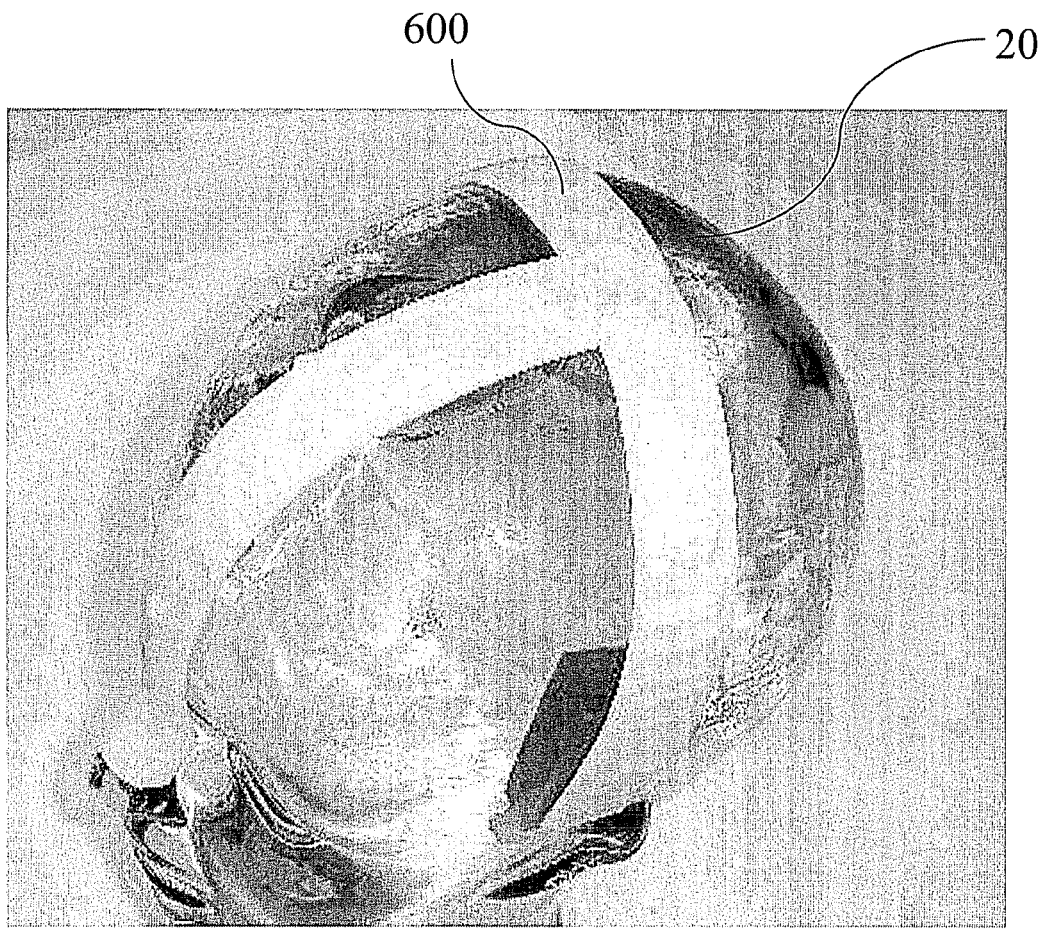
FIG. 9 is a scanned photograph showing a custom article according to the invention, fabricated using rapid prototyping technology and fitted to the glass head model shown in FIG. 2.
Figure 10:
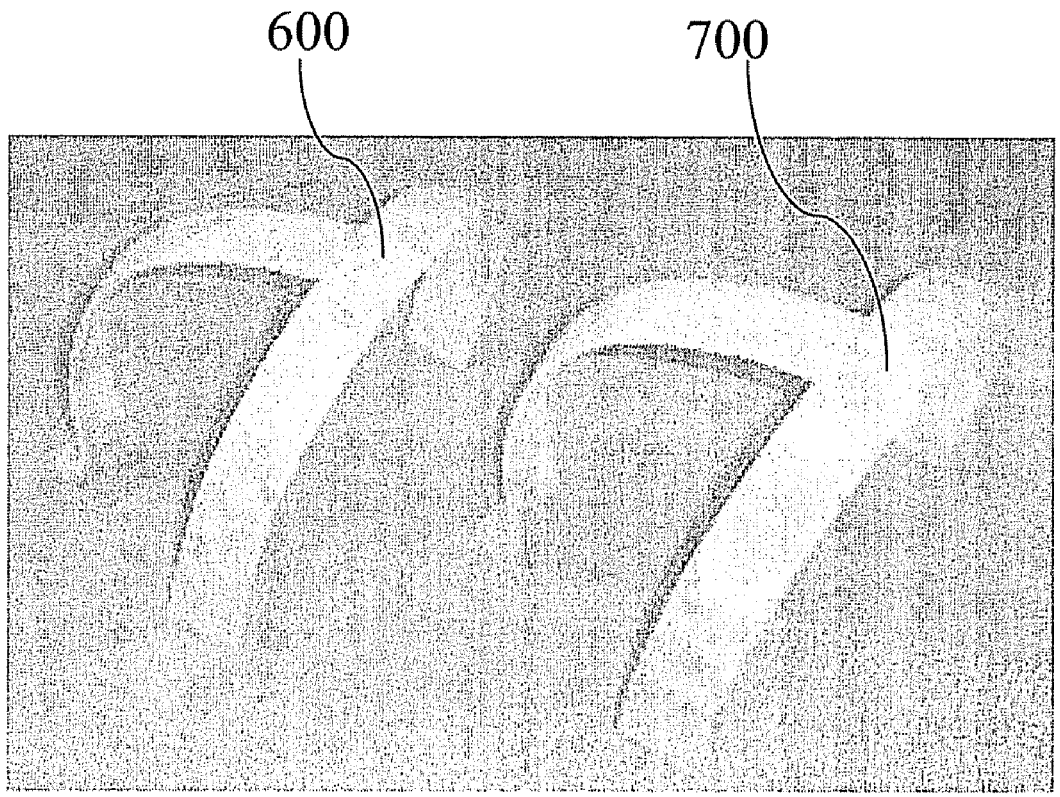
FIG. 10 is a scanned photograph showing custom articles fabricated by rapid prototyping techniques of 3D printing (left) and stereolithography (right), according to an embodiment of the invention.

Both of the rapid prototyping methods produced custom articles that precisely and uniquely fit onto the glass head model 20. FIG. 9 is a photograph showing an article 600 fabricated using stereolithography, and applied to the glass head model 20. The photograph in FIG. 10 shows a comparison of the articles 600 and 700 produced by the two fabrication methods. Units fabricated by stereolithography and three dimensional printing were very similar in appearance.

While the above specification contains many specifics, these should not be construed as limitations on the scope of the invention, but rather as examples of preferred embodiments thereof. Many other variations are possible. Accordingly, the scope of the invention should be determined not by the embodiments illustrated, but by the appended claims and their legal equivalents.

We claim:

1. A device for guiding a craniotomy procedure pre-planned using a virtual model of a head of a subject, comprising:
    a subject-specific article comprising at least one substantially rigid reference portion,
    said reference portion having dimensions matching a contour of a first exterior surface portion of the head of the subject to be treated, wherein said reference portion dimensions are derived from head surface dimensions of a virtual model of the head of the subject,
    said article rigidly and replaceably attachable to said first surface portion exclusive of fasteners anchored to tissue of the subject underlying said article upon attachment in one configuration, wherein said article upon attachment exclusively resides on a front of a head of the subject in said one configuration,
    said article including a probe guide emerging from one or more openings in said article, each opening being aligned with a preplanned trajectory for treating one or more target regions inside the head of the subject,
    said article further comprising at least one custom skin clip or retractor for attachment to at least one surface along a periphery of said one or more openings, and
    said one configuration providing a customized spatially unambiguous reference for alignment of said one or more openings along said preplanned trajectory for treating said target regions.

2. The device of claim 1, wherein said first exterior surface portion comprises an exterior surface portion selected from the group consisting of the nose, the eye socket, and the eyebrow ridge.

3. The device of claim 1, wherein an angle of said probe guide emerging from said opening is adjustable.

4. The device of claim 1, wherein said probe guide is oriented at a predetermined angle, said angle aligning said probe guide along said preplanned trajectory for treating said target regions when said article is in said one configuration.

5. The device of claim 4, said article further comprising at least one structure directing a biopsy or incision depth.

6. The device of claim 1, said article further comprising a stereotactic phantom device.

7. The device of claim 1, wherein said probe guide is separately fabricated and attached using a standardized attachment mechanism.

8. The device of claim 7, further comprising a craniotomy instrument fabricated for attachment using said standardized attachment mechanism.

9. The device of claim 8, wherein said craniotomy instrument is selected from a probe guide, a biopsy guide, an incision guide, and a stereotactic phantom device.

10. A method for pre-planning a craniotomy procedure, comprising the steps of:
    generating a virtual model of a head of a subject;
    identifying one or more target regions inside the head of the subject;
    determining a preplanned trajectory for treating said target regions;
    producing a subject-specific article comprising:
        at least one substantially rigid reference portion, said reference portion having dimensions matching a contour of a first exterior surface portion of the head of the subject to be treated, wherein said reference portion dimensions are derived from head surface dimensions of the virtual model of the head of the subject,
        said article rigidly and replaceably attachable to said first surface portion exclusive of fasteners anchored to tissue of the subject underlying said article upon attachment in one configuration, wherein said article upon attachment exclusively resides on a front of a head of the subject in said one configuration,
        said article including a probe guide emerging from one or more openings in said article, each opening being aligned with said preplanned trajectory for treating said one or more target regions inside the head of the subject,
        said article further comprising at least one custom skin clip or retractor for attachment to at least one surface along a periphery of said one or more openings, and
        said one configuration providing a customized spatially unambiguous reference for alignment of said one or more openings along said preplanned trajectory for treating said target regions;
    attaching said article to said head of said subject in said one configuration; and
    performing a craniotomy procedure on said target regions through said openings in said subject-specific article, said performing step comprising attaching at least one custom skin clip or retractor to at least one surface along said periphery of said opening.

11. The method of claim 10, further comprising the step of:
    checking for proper alignment of said article upon attachment to said subject using a stereotactic phantom device procedure before performing said craniotomy procedure on said target region.

12. The method of claim 10, wherein said subject-specific article further comprises a cut-out edge for making an incision along a preplanned course, and said performing step comprises making an incision through the scalp using said cut-out edge.

13. The method of claim 10, wherein said probe guide is separately fabricated and attached using a standardized attachment mechanism and said subject-specific article further comprises a craniotomy instrument fabricated for attachment using said standardized attachment mechanism.

14. The method of claim 13, wherein said performing step comprises sequentially attaching the probe guide and the craniotomy instrument to the subject-specific article and using the probe guide and the craniotomy instrument to treat said target regions along a preplanned trajectory.

15. A system for performing a craniotomy procedure, comprising:

an imaging system for generating a virtual model of a head of a subject;

a subject-specific article comprising:

a subject-specific article comprising at least one substantially rigid reference portion, said reference portion having dimensions matching a contour of a first exterior surface portion of the head of the subject to be treated, wherein said reference portion dimensions are derived from head surface dimensions of the virtual model of the head of the subject, said article rigidly and replaceably attachable to said first surface portion exclusive of fasteners anchored to tissue of the subject underlying said article upon attachment in one configuration, wherein said article upon attachment exclusively resides on a front of a head of the subject in said one configuration, said article including a probe guide emerging from one or more openings in said article, each opening being aligned with said preplanned trajectory for treating said one or more target regions inside the head of the subject, said article further comprising at least one custom skin clip or retractor for attachment to at least one surface along a periphery of said one or more openings, and said one configuration providing a customized spatially unambiguous reference for alignment of said one or more openings along said preplanned trajectory for treating said target regions; and a therapeutic, diagnostic or surgical device, wherein said device is physically guided to said target regions along said preplanned trajectory at least in part by said probe guide of said subject-specific article.

16. The system of claim 15, wherein said subject-specific article further comprises a plurality of external reference markers.

* * * * *